United States Patent
Kleffner et al.

(10) Patent No.: US 6,719,692 B2
(45) Date of Patent: Apr. 13, 2004

(54) ROTATING SURGICAL TOOL

(75) Inventors: Bernhard V. Kleffner, Wilhelmsdorf (DE); Micheal H. Mayer, Gräfelfing (DE); Charles Wing, Wurmlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 50 days.

(21) Appl. No.: 10/004,274

(22) Filed: Oct. 23, 2001

(65) Prior Publication Data

US 2002/0120197 A1 Aug. 29, 2002

Related U.S. Application Data

(63) Continuation of application No. PCT/EP00/02253, filed on Mar. 15, 2000.

(30) Foreign Application Priority Data

May 7, 1999 (DE) .......................................... 199 21 279

(51) Int. Cl.[7] .................................................. A61B 8/00
(52) U.S. Cl. ........................ 600/437; 606/169; 604/22
(58) Field of Search ................................. 600/437, 429, 600/426, 462, 561; 606/170, 171, 169, 130; 433/223, 215; 604/28; 128/898

(56) References Cited

U.S. PATENT DOCUMENTS

| | | | | |
|---|---|---|---|---|
| 3,976,077 A | * | 8/1976 | Kerfoot, Jr. | 606/107 |
| 4,478,580 A | * | 10/1984 | Barrut | 433/223 |
| 4,496,321 A | * | 1/1985 | Kumabe et al. | 433/215 |
| 5,230,338 A | * | 7/1993 | Allen et al. | 600/429 |
| 5,318,570 A | * | 6/1994 | Hood et al. | 606/99 |
| 5,935,143 A | * | 8/1999 | Hood | 606/169 |
| 5,980,545 A | * | 11/1999 | Pacala et al. | 606/170 |
| 6,432,058 B1 | * | 8/2002 | Sloth | 600/462 |
| 6,579,244 B2 | * | 6/2003 | Goodwin | 600/561 |
| 6,622,731 B2 | * | 9/2003 | Daniel et al. | 128/898 |
| 2003/0018297 A1 | * | 1/2003 | Constantz | 604/28 |

FOREIGN PATENT DOCUMENTS

| | | |
|---|---|---|
| DE | 43 04 570 | 8/1994 |
| DE | 195 22 310 | 1/1997 |
| DE | 299 08 259 | 7/1999 |
| EP | 0 284 055 | 9/1988 |
| JP | 07051277 | * 9/1993 |
| WO | 96/11638 | 4/1996 |

OTHER PUBLICATIONS

XP-002141166, "Orthopaedic Surgery", Zimmer Hall Surgical, 1992.
Patent Abstract of Japan, Abstract of Japanese Patent No. 07 051277, "Skull Boring Monitoring Device", p. 1128, vol. 95, No. 5, Feb. 28, 1995.

* cited by examiner

Primary Examiner—Dennis W. Ruhl
Assistant Examiner—Ruby Jain
(74) Attorney, Agent, or Firm—Barry R. Lipsitz; Douglas M. McAllister

(57) ABSTRACT

In order to optimize the handling of a rotating surgical tool for producing a depression in bone material, provision is made for an ultrasonic transducer which is capable of emitting and receiving ultrasonic waves to be arranged in the tool, and for the ultrasonic transducer to be connectable to an ultrasonic generator and to a receiver which generates signals in dependence upon the strength of the ultrasonic radiation received by the ultrasonic transducer and upon the length of time between the emission of ultrasonic radiation and the reception of reflected ultrasonic radiation, which are a measure of the condition of the bone material in the direction of emission.

14 Claims, 1 Drawing Sheet

ROTATING SURGICAL TOOL

The present disclosure relates to the subject matter disclosed in international patent application PCT/EP00/02253 of Mar. 15, 2000, which is incorporated herein by reference in its entirety and for all purposes.

BACKGROUND OF THE INVENTION

The invention relates to a rotating surgical tool for producing a depression in bone material.

Various rotating tools, for example, drills, milling cutters, reamers, etc., are known for making depressions in bone material. All of these tools are used for producing depressions of different shapes in the bone material, for example, drill holes for receiving bone screws. It is extremely important that these drill holes and depressions be placed in the desired manner in the bone, as in many cases only little bone material is available for fixing bone screws and other parts of implants. For example, in the area of the spine it is extremely difficult to place pedicle screws in the body of the vertebra such that, on the one hand, they are fixed in the desired manner in the body of the vertebra and, on the other hand, do not cause any injuries.

To date, it has essentially been possible for this to be carried out within the operator's field of vision or, at the most, under radiological supervision, which may have involved increased exposure of the patient and operator to radiation.

The object of the invention is to so design a generic tool that it enables depressions to be made in a controlled manner in the desired position and direction in bone material.

SUMMARY OF THE INVENTION

This object is accomplished with a rotating surgical tool of the kind described at the outset, in accordance with the invention, by an ultrasonic transducer being arranged in the surgical tool, the ultrasonic transducer being capable of emitting and receiving ultrasonic waves and being connectable to an ultrasonic generator and a receiver, the receiver generating signals in dependence upon the strength of the ultrasonic radiation received by the ultrasonic transducer and upon the length of time between the emission of ultrasonic radiation and the reception of reflected ultrasonic radiation, the signals being a measure of the condition of the bone material in the direction of emission.

The ultrasonic radiation emitted by the transducer in the rotating tool penetrates the surrounding bone structures and is reflected there, in particular, at the surfaces of the bone material and at inhomogeneities in the bone material, for example, at surfaces at which the structure of the bone material changes. The reflected ultrasonic radiation is picked up by the transducer, and information on the condition of the bone material adjacent to the tool, in particular, on the layer thickness of the bone material and possibly also on structural changes in the bone material, is derivable from the strength of the picked-up signal and the time lapse since emission of the ultrasonic radiation. The operator can use this information to check the position of the tool in the bone and thus the position of the depression made by the tool. Separate transducers may be provided for the emission and reception of the ultrasonic radiation, but it is also possible to emit the ultrasonic radiation and subsequently pick up the reflected radiation again with the same transducer. This can be carried out with, for example, a so-called pulse-echo technique.

It is expedient for the ultrasonic transducer to be arranged in the area of the distal end of the tool so that the area in front of the distal end of the tool is "seen" by the ultrasonic radiation emitted by the tool. The operator is thus given information on the condition of the bone material in the cutting direction, and he is thereby enabled to control the direction of advance of the tool accordingly.

A particularly expedient embodiment is obtained when the ultrasonic transducer is arranged in the tool such that the direction in which it emits and receives the ultrasonic waves is at an incline to the axis of rotation, for example, at an angle of inclination of between 30° and 60°, in particular, in the order of magnitude of approximately 45°. In such an embodiment, the ultrasonic radiation is emitted on the outer surface of a cone which opens in the distal direction, and in this way the operator receives information not only exactly in the direction of advance of the rotating tool but over the entire rotary angle of the tool in an area located in front of the tool in the distal direction. This results in an optimal orientation with regard to the bone areas still to be worked on.

In a preferred embodiment of the invention, provision is made for the tool to comprise an inside receiving space for the ultrasonic transducer, which communicates with a channel extending in the tool as far as the proximal end thereof. Connection lines for the ultrasonic transducer may pass through this channel.

In a preferred embodiment, the tool is a drill with a conical cutting surface, and the ultrasonic transducer is arranged in the area of the conical cutting surface. With such a drill, the operator can see precisely during the drilling operation whether he is at an adequate distance from all delimitations of the bone as the drill advances further, so that the drill hole will definitely extend in the bone material and will not unintentionally penetrate cavities or other tissue.

It is particularly expedient for the tool to comprise a sensor for its angular position, and for the sensor to feed a signal corresponding to the angular position to the receiver which thus generates the signals for the condition of the bone in dependence upon the angular position of the tool. The operator is thus given a comprehensive picture of the condition of the bone material in front of the tool, namely in all angular directions. At the same time, the ultrasonic transducer forms a camera which is arranged on a rotatable carrier and sweeps over the entire area located in front of the tool in all directions.

Provision may also be made for an optical display device which indicates the signals generated by the receiver for the condition of the bone to be associated with the receiver. One can thus read off directly from such a display device the condition of the bone in the direction of emission of the ultrasonic radiation, the available wall thickness of the bone here and any structural changes that might occur.

It is particularly advantageous for cross sections through the tool and the adjacent bone material to be able to be represented on the optical display device, with the condition of the bone material being determined by the signals generated by the receiver. These cross sections simultaneously show the signals generated by the receiver, which occur with a different angular position of the tool, so that one is simultaneously given information on the condition of the bone over the entire angular area.

In particular, provision may be made for the illustrated cross-sectional area to be a conical surface which opens in the distal direction, and the axis of which coincides with the axis of rotation of the tool. A display range which scans the area in front of the tool and thus indicates the condition of the bone in the area which the tool will later penetrate is thus shown.

Cross sections of implants which show the way in which certain implants are to be arranged in the bone after the implantation can also be faded in on the optical display device. With a knowledge of the shape of the implant and the desired position of the implant, it is thus possible for the operator to place depressions, for example, drill holes such that their position corresponds to the shape and position of the implant. The image of the implant can be produced from a data memory in which the data representing this implant are stored. From these data, the image can be superimposed on the image resulting from the ultrasonic signals.

A warning device operating, for example, optically or acoustically can also be associated with the receiver to warn the operator that the wall thickness of the bone material in the area to be worked on is falling below a certain level, i.e., that he risks perforating it.

The following description of a preferred embodiment of the invention serves in conjunction with the drawings to explain the invention in further detail.

DETAILED DESCRIPTION OF THE INVENTION

Figure 1:
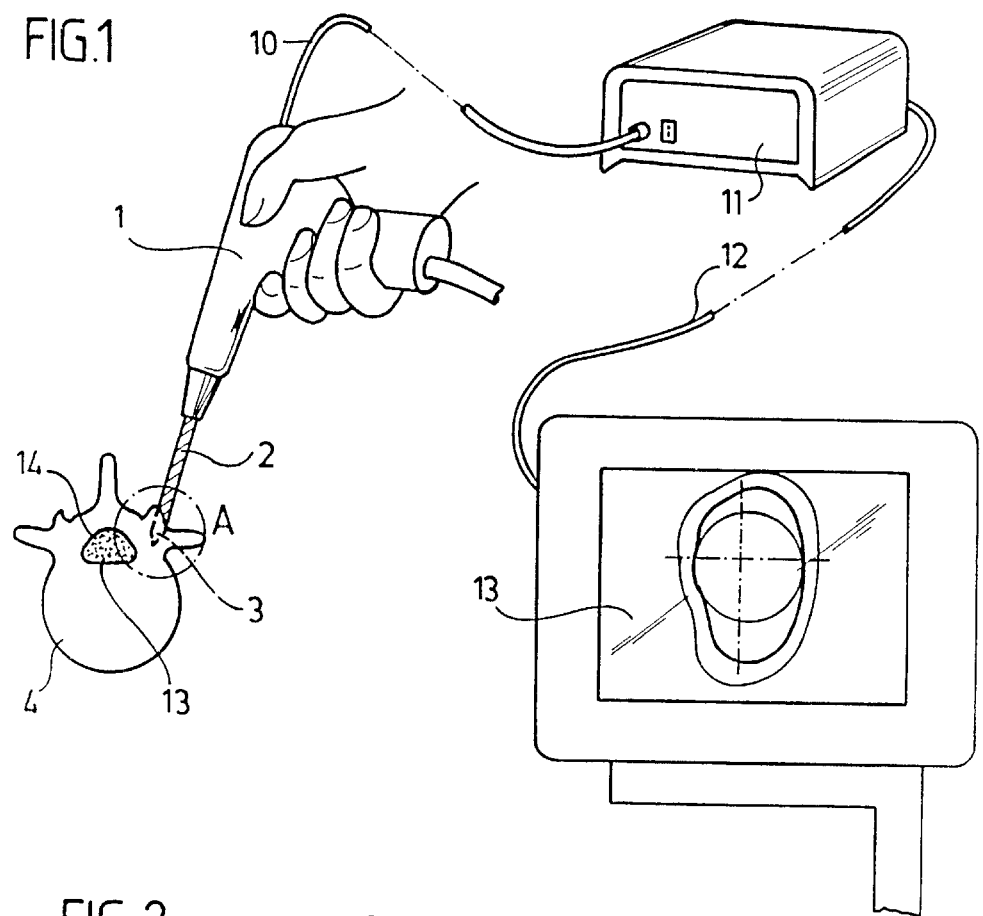
FIG. 1 is a schematic view of a drill applied to the body of a vertebra with an ultrasonic monitoring device with optical display.
Figure 2:
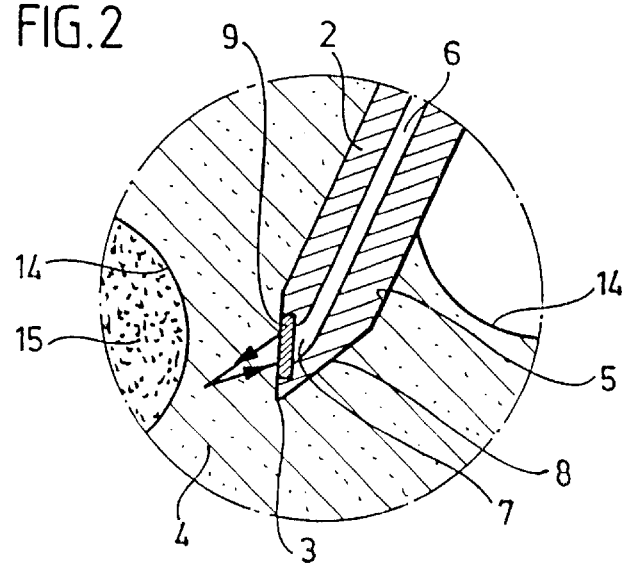
FIG. 2 is an enlarged sectional view in the area A in FIG. 1 with a drill equipped with an ultrasonic transducer.

The invention will be explained hereinbelow with reference to a drill, by way of example, but, in principle, the invention can also be employed in other rotating cutting tools such as, for example, milling cutters, reamers, trephines, etc., by means of which the bone material is cut away by rotational motion, in particular, to produce drill holes and other depressions.

A surgical hand drilling machine 1 is equipped with a twist drill 2 which is rotated by a drive inside the hand drilling machine 1 about its longitudinal axis and with its bit 3 produces a drill hole 5 in a bone 4, in the illustrated embodiment in the pedicle area of a vertebra.

In contrast to a conventional twist drill, this twist drill 2 is provided with an inside channel 6 extending from the proximal end into the distal end area which terminates in a receiving space 7 located immediately behind the conical cutting surface 8 of the twist drill 2. Arranged in this receiving space 7 is an ultrasonic transducer 9 which can emit ultrasonic radiation essentially perpendicularly to the cutting surface 8 and can receive ultrasonic radiation impinging upon it from this direction. This may be a single ultrasonic transducer 9 or two separate ultrasonic transducers which are each designed for emission or reception of ultrasonic radiation.

The ultrasonic transducer is connected by a line, not shown in greater detail in the drawings, which passes through the inside channel 6, to a connection line 10 which starts at the hand drilling machine 1 and terminates at a transmitter and receiver 11, which, in turn, is connected by a connection line 12 to a display device 13. The transmitter and receiver 11 can operate, for example, as a so-called pulse-echo system and can generate and receive ultrasonic radiation with frequencies in the order of magnitude of 15 MHz. This ultrasonic radiation is emitted in the form of a pulse by ultrasonic transducer 9 into the surrounding bone 4 and reflects there at inhomogeneities and at interfaces, for example, at the interface 14 to the medullary space 15 of the vertebra.

The reflected radiation subsequently impinges again on the ultrasonic transducer 9 where it is converted into an electric signal which is fed to the transmitter and receiver 11. The size of the signal corresponding to the reflected radiation depends on the strength of the reflection at the inhomogeneity, and the length of time between the emission of the pulse and the reception of the reflected radiation depends on the thickness of the bone material up to an interface and on the condition of the bone material, as this condition influences the speed of propagation of the ultrasonic radiation.

It is thus possible, with knowledge of the structure of the bone, to determine the distance at which interfaces and inhomogeneities of the bone are located from the ultrasonic transducer, in both the emitting and receiving directions of the ultrasonic transducer. This ultrasonic transducer rotates together with the twist drill 2 and when emitting and receiving the ultrasonic radiation can therefore sweep over the outer surface of a cone, which is formed by a cone arranged coaxially with the axis of rotation of the twist drill 2 and opening in the distal direction. The reflection signals fed to the transmitter and receiver 11 are thus a measure of the condition of the bone and the thickness of the bone material on this conical outer surface, i.e., in an area which is located in front of the twist drill 2 in the distal direction and which the twist drill 2 will enter upon further cutting.

The signals received by the transmitter and receiver 11 can be represented on the display device 13 so that starting from the position of the twist drill 2 the area of the bone around the twist drill 2, which is covered by the ultrasonic radiation, is represented and the operator is thus given an optical indication as to the condition of the bone material around the twist drill 2 in an area located in front of the twist drill in the distal direction, for example, the size of the distance to the next cavity or to an interface of the bone. This enables the operator to direct the twist drill 2 such that upon penetrating further into the bone 4, it always remains centered as exactly as possible in the bone material and keeps at a sufficient distance from the interfaces of the bone. In this way, it is also possible to direct the twist drill 2 into areas of particularly solid bone material as the reflected ultrasonic signals also provide information on the consistency of the bone material. For example, the speed of propagation of the ultrasonic waves in the bone tissue changes when the bone tissue is differently structured.

There is thus installed in the bit of the twist drill 2 an ultrasonic camera with receiver, which observes the area located in front of the bit of the twist drill 2 and thus offers the operator information on the bone areas into which the twist drill 2 will move upon further penetration.

What is claimed is:

1. Mechanically rotating surgical power tool for cutting bone material, comprising:
    an ultrasonic transducer being arranged in a rotating portion of said surgical power tool, said ultrasonic transducer being capable of rotating with said rotating portion and of emitting and receiving ultrasonic waves while rotating and being connectable to an ultrasonic generator and a receiver,
    said receiver generating signals in dependence upon a strength of ultrasonic radiation received by the ultrasonic transducer and upon a length of time between emission of ultrasonic radiation and reception of reflected ultrasonic radiation, said signals being a measure of a condition of the bone material in a direction of emission.

2. Tool in accordance with claim 1, wherein the ultrasonic transducer is arranged in an area of a distal end of the tool.

3. Tool in accordance with claim 2, wherein the ultrasonic transducer is arranged in the tool such that the direction in which it emits and receives the ultrasonic waves is at an incline to an axis of rotation of said tool.

4. Tool in accordance with claim 1, wherein the ultrasonic transducer is arranged in the tool such that the direction in which it emits and receives the ultrasonic waves is at an incline to an axis of rotation of said tool.

5. Tool in accordance with claim 4, wherein the angle of inclination lies between 30° and 60°.

6. Tool in accordance with claim 1, wherein the tool comprises an inside receiving space for the ultrasonic transducer, which is in communication with a channel extending in the tool as far as a proximal end thereof.

7. Tool in accordance with claim 1, wherein the tool is a drill with a conical cutting surface, and wherein the ultrasonic transducer is arranged in an area of the conical cutting surface.

8. Tool in accordance with claim 7, wherein the tool includes a sensor for its angular position, and wherein said sensor feeds a signal corresponding to the angular position to the receiver which thus generates the signals for the condition of the bone in dependence upon the angular position of the tool.

9. Tool in accordance with claim 1, wherein the tool includes a sensor for its angular position, and wherein said sensor feeds a signal corresponding to the angular position to the receiver which thus generates the signals for the condition of the bone in dependence upon the angular position of the tool.

10. Tool in accordance with claim 1, wherein an optical display device which indicates the signals generated by the receiver for the condition of the bone is associated with the receiver.

11. Tool in accordance with claim 10, wherein cross sections through the tool and the adjacent bone material are able to be illustrated on the optical display device, and the condition of the bone material is determined by the signals generated by the receiver.

12. Tool in accordance with claim 11, wherein the illustrated cross-sectional surface is a conical surface which opens in a distal direction, and an axis of which coincides with an axis of rotation of the tool.

13. Tool in accordance with claim 10, wherein, in addition, illustrations of implants are able to be made visible on the optical display device.

14. Tool in accordance with claim 1, wherein a warning device which generates a warning signal in dependence upon the strength of the bone is associated with the receiver.

* * * * *

UNITED STATES PATENT AND TRADEMARK OFFICE
CERTIFICATE OF CORRECTION

PATENT NO. : 6,719,692 B2
DATED : April 13, 2004
INVENTOR(S) : Kleffner et al.

It is certified that error appears in the above-identified patent and that said Letters Patent is hereby corrected as shown below:

<u>Title page,</u>
Item [75], Inventors, the second inventor should read
-- H. Michael Mayer --; and
the city of residence for the third inventor, Charles Wing, should read
-- Tuttlingen --

Signed and Sealed this

Twenty-ninth Day of June, 2004

JON W. DUDAS
*Acting Director of the United States Patent and Trademark Office*